(12) United States Patent
Lochmann

(10) Patent No.: US 9,852,333 B2
(45) Date of Patent: Dec. 26, 2017

(54) SYSTEM AND METHOD FOR DETECTING A USER-DEPENDENT STATE OF A SPORT OBJECT

(75) Inventor: Matthias Lochmann, Neunkirchen am Brand (DE)

(73) Assignee: FRAUNHOFER—GESELLSCHAFT ZUR FÖRDERUNG DER ANGEWANDTEN FORSCHUNG E.V., München (DE)

( * ) Notice: Subject to any disclaimer, the term of this patent is extended or adjusted under 35 U.S.C. 154(b) by 270 days.

(21) Appl. No.: 14/345,974

(22) PCT Filed: Sep. 20, 2011

(86) PCT No.: PCT/EP2011/066264
§ 371 (c)(1),
(2), (4) Date: Jun. 29, 2014

(87) PCT Pub. No.: WO2013/041124
PCT Pub. Date: Mar. 28, 2013

(65) Prior Publication Data
US 2014/0330411 A1    Nov. 6, 2014

(51) Int. Cl.
| | | |
|---|---|---|
| A63F 9/24 | (2006.01) |
| G06K 9/00 | (2006.01) |
| G01S 17/06 | (2006.01) |
| G01S 19/19 | (2010.01) |
| G01S 5/00 | (2006.01) |
| G01S 13/06 | (2006.01) |
| G06F 19/00 | (2011.01) |
| G09B 19/00 | (2006.01) |

(52) U.S. Cl.
CPC ........ *G06K 9/00342* (2013.01); *G01S 5/0018* (2013.01); *G01S 13/06* (2013.01); *G01S 17/06* (2013.01); *G01S 19/19* (2013.01); *G06F 19/3481* (2013.01); *G09B 19/0038* (2013.01)

(58) Field of Classification Search
None
See application file for complete search history.

(56) References Cited

U.S. PATENT DOCUMENTS

| | | | | |
|---|---|---|---|---|
| 5,912,700 A * | 6/1999 | Honey | ............... | A63B 71/0605 348/157 |
| 6,157,898 A * | 12/2000 | Marinelli | ............... | A63B 43/00 473/569 |
| 7,978,081 B2 * | 7/2011 | Shears | ................. | A61B 5/1127 340/573.1 |
| 2002/0082775 A1* | 6/2002 | Meadows | .............. | A63B 57/00 701/472 |

(Continued)

FOREIGN PATENT DOCUMENTS

| | | |
|---|---|---|
| EP | 2025372 | 2/2009 |
| WO | 99/49279 A1 | 9/1999 |

(Continued)

*Primary Examiner* — Paul A D'Agostino
(74) *Attorney, Agent, or Firm* — Mannava & Kang, P.C.; Arash Behravesh

(57) ABSTRACT

The invention relates to a system for detecting a user-dependent state of a sports object, comprising a detection device (101) for detecting a plurality of positions of the sports object, and a determination device (103) for determining the state of the sports object based on the plurality of positions detected.

19 Claims, 7 Drawing Sheets

(56) References Cited

U.S. PATENT DOCUMENTS

| | | | | |
|---|---|---|---|---|
| 2005/0233815 A1* | 10/2005 | McCreary | .......... | A63B 24/0021 |
| | | | | 473/131 |
| 2005/0259002 A1* | 11/2005 | Erario | ................ | A63B 24/0021 |
| | | | | 342/357.61 |
| 2008/0220891 A1* | 9/2008 | Gobush | .............. | A63B 69/3658 |
| | | | | 473/221 |
| 2009/0048044 A1* | 2/2009 | Oleson | ............... | A63B 24/0062 |
| | | | | 473/570 |
| 2010/0144456 A1* | 6/2010 | Ahern | .................... | A63B 57/00 |
| | | | | 473/222 |

FOREIGN PATENT DOCUMENTS

| | | |
|---|---|---|
| WO | WO 01/10517 | 2/2001 |
| WO | WO 02/14894 | 2/2002 |
| WO | WO 2010/065886 | 6/2010 |

\* cited by examiner

SYSTEM AND METHOD FOR DETECTING A USER-DEPENDENT STATE OF A SPORT OBJECT

PRIORITY

The present application claims priority under 35 U.S.C. §371 to PCT Application PCT/EP2011/066264, filed on Sep. 20, 2011, the disclosures of which are hereby incorporated by reference in their entireties.

The present invention relates to a system and a method for detecting a user-dependent state of a sports object.

Human movement is a complex biomechanical sequence. In this regard, by way of example, a sportsperson who uses a sports object such as a ball or a throwing implement, for instance, in the context of training, has to practice those movement sequences which lead to an optimum sports result. In this context, it is also important to find out whether the sportsperson can put the playing object into a specific state of movement, such as ball passing velocity, for instance.

Therefore, the problem addressed by the present invention is that of providing a concept for detecting a user-dependent state of a sports object.

This problem is solved by means of the features of the independent claims. Advantageous developments are the subject matter of the dependent claims, of the description and of the figures.

The present invention is based on the insight that the above problem can be solved by observation of the playing object. In this regard, by way of example, the ball velocity or the ball acceleration or the ball residence duration at a sportsperson can be detected with the aid of a plurality of observed positions of a ball within a predetermined time interval.

In accordance with a first aspect, the invention relates to a system for detecting a user-dependent state of a sports object, comprising a detection device for detecting a plurality of positions of the sports object and a determination device for determining the state of the sports object on the basis of the detected plurality of positions.

In accordance with one embodiment, the sports object is a ball or a puck. The user is a sportsperson.

In accordance with one embodiment, the state of the sports object is one of the following states: residence duration of the sports object at a user, velocity, in particular translational velocity or rotational velocity, of the sports object, momentum, in particular angular momentum or translational momentum, of the sports object, direction of movement of the sports object, acceleration, in particular positive or negative acceleration, of the sports object.

In accordance with one embodiment, the sports object is designed to emit a position signal, in particular a global positioning signal, and wherein the detection device is designed to receive the position signal in order to determine the plurality of positions. The detection device is designed to receive the position signal and to determine the plurality of positions of the playing object on the basis of the received position signal. For receiving the position signal, the detection device can comprise a receiving antenna that receives the position signal. The detection device can furthermore be designed to process the received position signal in order to detect the positions of the playing object.

In accordance with one embodiment, the detection device is designed to receive a reflection signal reflected at the sports object, in particular a radar signal or a laser signal, and to determine the plurality of positions on the basis of the reflected reflection signal.

In accordance with one embodiment, the detection device is designed to emit a transmission signal, in particular a radar signal or a laser signal, in order to generate the reflection signal. The playing object can have for this purpose a reflective surface, for example, which can be metallic, in order to reflect a radar signal.

In accordance with one embodiment, the determination device is designed to determine a first instant of an acceptance of the sports object by the user and a second instant of a release of the sports object by the user, in order to determine a residence duration of the sports object at the user as the user-dependent state of the sports object.

In accordance with one embodiment, the determination device is designed to determine a third instant of a transfer of the sports object by the user between the first instant and the second instant, in order to determine a first sub-residence duration between the first instant and the third instant and a second sub-residence duration between the third instant and the second instant. The third instant as a further user-dependent state can be determined, for example, by a player transferring the ball from one foot to the other.

In accordance with one embodiment, the determination device is designed, for the purpose of determining the user-dependent state, to determine an instant of an acceptance of the sports object by the user by detection of a negative acceleration of the sports object with the aid of a temporal profile of the plurality of positions of the sports object.

In accordance with one embodiment, the determination device is designed, for the purpose of determining the user-dependent state, to determine an instant of a release of the sports object by detection of a positive acceleration of the sports object with the aid of a temporal profile of the plurality of positions of the sports object.

In accordance with one embodiment, the system comprises a sports object provider, in particular a ball provider, for dispensing the sports object.

In accordance with one embodiment, the system comprises a sports object catcher for catching the sports object after a sports object release by the user.

In accordance with one embodiment, the sports object catcher is a ball goal or a sensor wall.

In accordance with one embodiment, the detection device is designed to store the detected plurality of positions.

In accordance with one embodiment, the system comprises an indication device for indicating the detected plurality of positions or for projecting a projection region onto a playing area, in particular around a further player.

In accordance with one embodiment, the determination device is designed to compare the user-dependent state with a reference state in order to assess the user-dependent state.

In accordance with one embodiment, the detection device is designed for detecting an actual position of the playing object, and the determination device is designed for determining a desired position of the playing object. The indication device is designed for indicating information relating to the desired position if the actual position differs from the desired position.

The information relating to the desired position can comprise an indication of the desired position itself or an indication of the fact that the desired position has not yet been reached, or an indication of a direction of the desired position. In order to ascertain whether the actual position differs from the desired position, the determination device can compare the actual position with the desired position. In this case, the actual position and the desired position can be present in the form of digital position data.

In accordance with one embodiment, the determination device is designed to determine a predetermined position of the playing object, in particular a predefinable position of the playing object, as the desired position. The predetermined position of the playing object can be selected from a plurality of possible desired positions, for example. This selection can be random or deterministic. The predetermined, deterministic position can be predefined with the aid of a rule, for example.

In accordance with one embodiment, the playing object is a ball, and the determination device is designed to determine, in particular select, a sensor region of a sensor wall as the desired position. In accordance with one embodiment, the sensor wall is an element of the system. In accordance with another embodiment, the sensor wall is not an element of the system. The sensor wall can have at least one sensor, for example a pressure sensor, for detecting the ball. In accordance with one embodiment, however, the sensor wall can be formed in such a way that the arrival of the ball is detectable optically, for example, by an indentation or protrusion of the sensor wall, for example.

In this way, by way of example, a region of the sensor wall which represents a goal can be indicated to a soccer player as the desired position of the ball. In this way, the soccer player can rapidly practice different ball shooting exercises.

In accordance with one embodiment, the system can comprise one or more ball providers that release a playing object, for example a ball. The ball provider can be designed to release the ball in a predetermined direction, for example toward the player. The indication device can be formed by the sensor wall, which indicates the sensor region as the desired position.

In accordance with one embodiment, the determination device is designed to determine the desired position in a manner dependent on the actual position of the playing object. This enables a dynamic determination of the desired position in a manner dependent on, for example, playing events on a playing area.

In accordance with one embodiment, the determination device is designed to determine the desired position in a manner dependent on the actual position of the playing object and a geometrical characteristic of a region, in particular of a playing area, within which the playing object is movable, or the desired position in a manner dependent on the actual position of the playing object in relation to a geometric characteristic of the playing area, in particular a goal center. In this regard, by way of example, it is possible to determine the desired position as a connecting line between goal center and ball in a manner dependent on a ball position.

In accordance with one embodiment, the determination device is designed to determine the desired position as a sequence of progressive auxiliary positions. The progressive sequence of the auxiliary positions simplifies the step-by-step process of attaining a final desired position, since, for example, relatively small movement steps can be practiced.

In accordance with one embodiment, the detection device is designed to determine a further actual positions from a further playing object, and the determination device is designed to determine the desired position of the playing object in a manner dependent on the further actual position, in particular relative to the further actual position of the further playing object.

In accordance with one embodiment, the determination device is designed to determine the desired position with the aid of a predefined rule that links the desired position to an actual position. The rule can link for example the desired position of a player in relation to the further actual position of a further player.

In accordance with one embodiment, the detection device is designed to determine a plurality of further actual positions from a plurality of further playing objects, and the determination device is designed to determine the desired position of the playing object in a manner dependent on the plurality of further actual positions. The plurality of further actual positions can be determined for example by actual positions of players of a playing team. In this way, it is possible to determine and/or indicate the desired position of an individual player in relation to the playing team.

In accordance with one embodiment, the determination device is designed to determine a centroid, in particular a geometrical or weighted centroid, of the further actual positions and to determine the desired position in a manner dependent on the centroid, in particular relative to the centroid. The geometrical centroid can be determined for example with the aid of any algorithm known per se which makes it possible to determine a geometrical centroid. The weighted centroid can be for example a geometrical centroid of—in accordance with one embodiment—weighted actual positions of the further playing objects. In the course of the weighting it is possible to express for example the importance of a player, for example of a goalkeeper, for a specific playing situation.

In accordance with one embodiment, the determination device is designed to determine the desired position in a manner dependent on the geometrical centroid with the aid of a predefined rule that links desired positions to geometrical centroids. Said rule can be created with the aid of empirical values, for example.

In accordance with one embodiment, the indication device is designed to indicate as information relating to the desired position the desired position itself or information relating to the location of the desired position with respect to a location of the playing object, in particular relating to a direction with respect to the desired position, or as information relating to a difference between the actual position and the desired position. The difference can be indicated for example by an acoustic signal, for example a beat or a frequency-variable signal, the beat frequency or the signal frequency being directly dependent on the difference.

In accordance with one embodiment, the indication device is designed to indicate the information relating to the desired position acoustically, optically, acousto-optically, in a tactile manner, in particular by means of a vibration or a pressure. For this purpose, it is possible that the indication device can be carried by the user, for example, in order to generate a, for example tactile, signal which indicates to the user, for example player, the information relating to the desired position. However, the indication device can comprise a screen or be designed to project the information by means of the projection onto a projection surface, for example onto a playing area or onto a visor plate of a helmet visor.

In accordance with one embodiment, the playing object is a playing ball, in particular a soccer ball or a table tennis ball or a tennis ball or a rugby ball, or a puck, and the indication device comprises a sensor wall for detecting the playing object arriving at the sensor wall, and the indication device is designed to indicate a region of the sensor wall as information relating to the desired position by visual highlighting, in particular by luminous emission or illumination of the region, or by acoustic highlighting. The sensor wall can comprise for example features of the abovementioned sensor wall or correspond to the abovementioned sensor wall.

In accordance with one embodiment, the indication device is designed to indicate the information relating to the desired position on an electronic display. The determination device can be designed to suitably actuate the display.

In accordance with one embodiment, the indication device is designed to actuate the display of a Smartphone for indicating the information relating to the desired position.

In accordance with one embodiment, both the detection device and/or the determination device and/or the indication device can be realized on such a Smartphone for example using software by means of an application program.

In accordance with one embodiment, the indication device is designed to project the information relating to the desired position onto a playing area by means of a light, in particular to project it by means of a laser projection or an LED projection.

In accordance with one embodiment, the determination device is designed to determine the desired position in a manner dependent on a body parameter, in particular heart rate, heart rate variability, respiratory frequency, body temperature, blood value parameters such as sugar concentration or oxygen concentration. The body parameters can be determined by means of contactless sensors, for example, and be emitted to the detection device, for example.

In accordance with one embodiment, the determination device comprises at least one position determining device, in particular a position transmitter, for detecting the actual position. Such a position transmitter can be accommodated for example on a player or in a ball. Generally, this embodiment makes it possible that the system according to the invention can be carried by a user.

In accordance with one embodiment, the system comprises a plurality of detection devices for detecting the actual position.

In accordance with a further aspect, the invention relates to a method for detecting a user-dependent state of a sports object, comprising detecting a plurality of positions of the sports object, and determining the state of the sports object on the basis of the detected plurality of positions.

Further features of the method are directly evident from the functionality of the system or of a feature of the system.

In accordance with one embodiment, the method can be performed by the system.

In accordance with a further aspect, the invention relates to a computer program comprising a program code for performing the method according to the invention if the program code is executed on a computer.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

Further exemplary embodiments of the invention are explained in greater detail with reference to the accompanying drawings, in which.

It is to be understood that both the foregoing general description and the following detailed description are exemplary and explanatory only, and are intended to provide an explanation of various embodiments of the present teachings.

Figure 1:
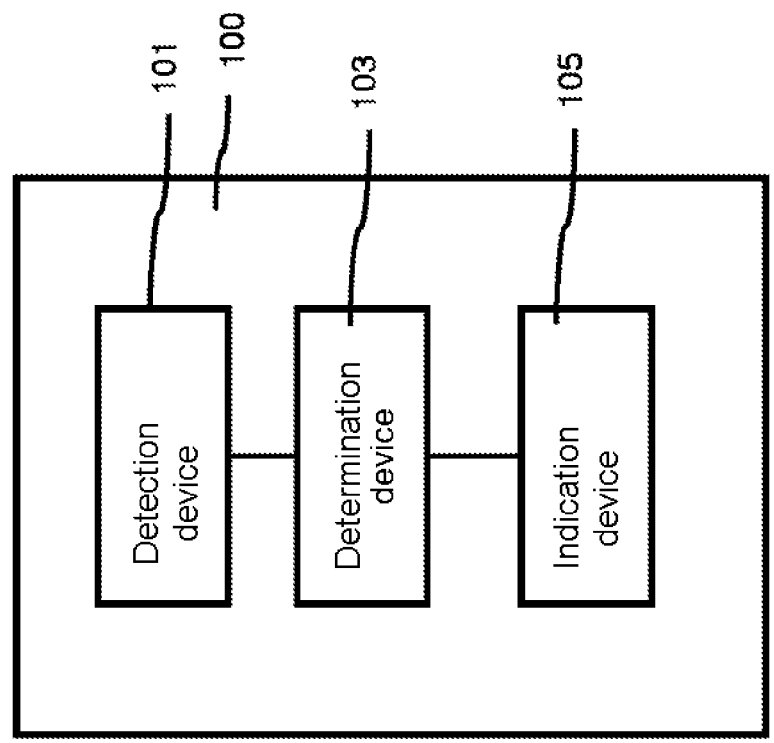
FIG. 1 shows a block diagram of a system for supporting a movement exercise with a playing object in accordance with one embodiment.

FIG. 1 shows a block diagram of a system 100 for detecting a user-dependent state of a sports object. The system 100 comprises a detection device 101 for detecting a plurality of positions of the sports object, and a determination device 103 determining the state of the sports object on the basis of the detected plurality of positions.

The state of the sports object can be one of the following states: residence duration of the sports object at a user, velocity, in particular translational velocity or rotational velocity, of the sports object, momentum, in particular angular momentum or translational momentum, of the sports object, direction of movement of the sports object, acceleration, in particular positive or negative acceleration, of the sports object.

Optionally, the system can comprise an indication device 105. The indication device 105 can be provided for indicating the detected plurality of positions, for example on a display.

Alternatively or additionally, the indication device 105 can be designed to project/cast a projection region onto a playing area. If the sports object is a ball and the state of the sports object is a residence duration of the ball at a player on a playing area, then the indication device 105 can be designed to project a projection region, for example a circle, around a further player onto the playing area in order to indicate to the further player that he is intended to remain within the projection region. The projection can be ended after a predetermined time of the residence duration, for example after a residence duration of 1 second or 2 seconds, in order to indicate to the further player that he can attack the player. It is thereby possible to simulate a real playing situation.

Figure 2:
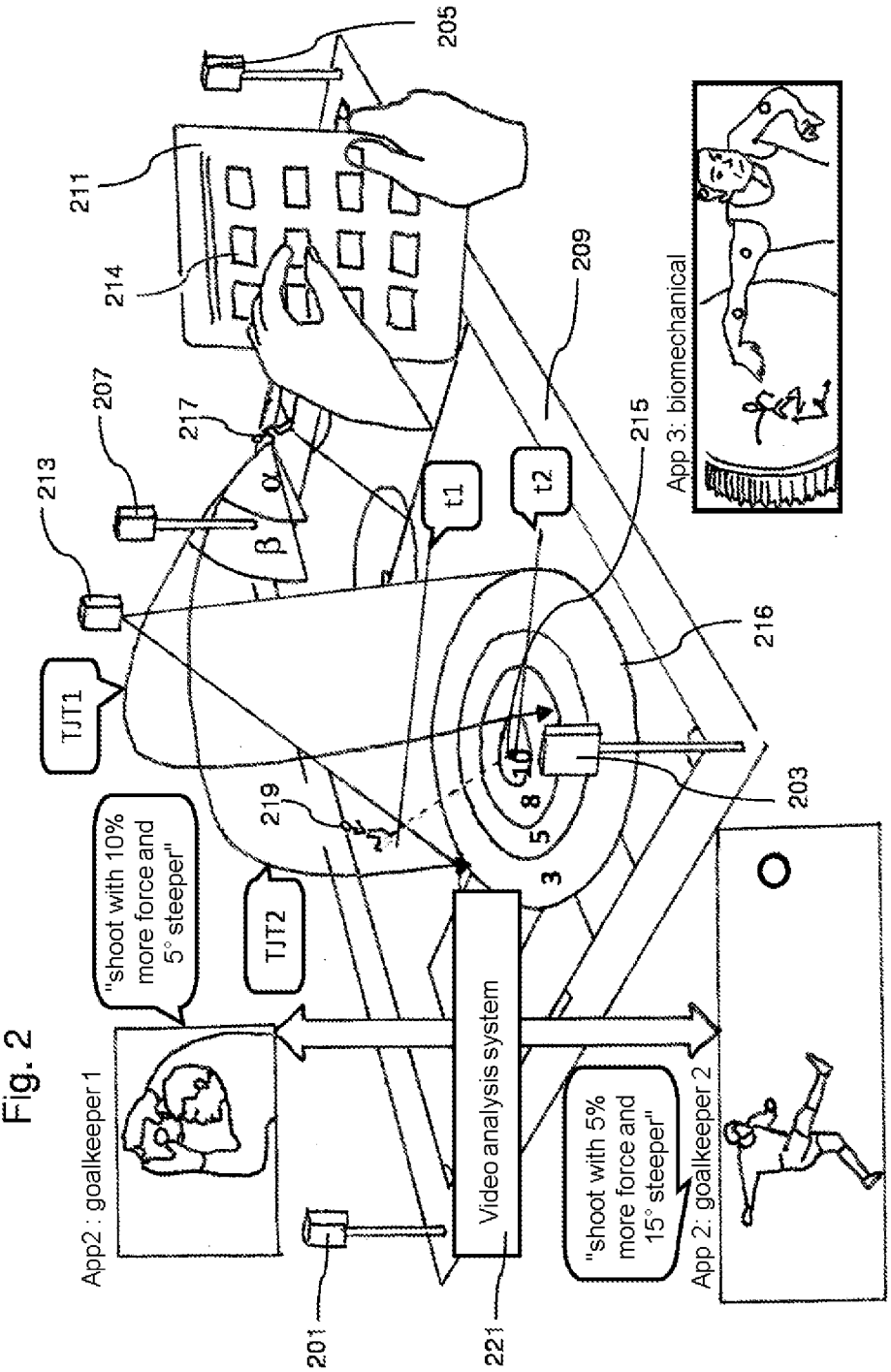
FIG. 2 shows a system for supporting a movement exercise in accordance with one embodiment.

FIG. 2 shows a system for supporting a movement exercise with a playing object, which is a soccer ball, for example. The system comprises a position localization system having a plurality of detection devices 201, 203, 205 and 207 (PLS1, PLS2, PLS3, PLS4) arranged at a distance from one another, for example in corners of a soccer pitch 209. However, the system can comprise only one, two or three or more than 4 detection devices.

The system furthermore comprises a determination device 211 for determining an actual position of the playing object, which actual position corresponds to the current actual position of the playing object. The determination device can be realized for example on a Smartphone by means of an application program, with a plurality of application fields 214, each enabling a desired position to be selected. The determination device 211 can, however, also be a separate computer or a computer cluster.

The system furthermore comprises an indication device 213 for indicating information relating to the desired position, provided that the actual position differs from the desired position. The desired position 215 can lie for example in a region 216 of the playing area 209. The indication device 213 can be designed, for example, to project concentric circles around the desired position 215 onto the playing area in order to indicate the desired position to a goalkeeper 217, for example. The actual position of the playing object can correspond for example, to the actual position of the goalkeeper 217. If a further player 219 is situated on the playing area 209, for example, then the desired position 215 can be determined and/or indicated in a manner dependent on an actual position of the further player 219. For this purpose, the further player 219 can be equipped with a transmitter which emits a position of the further player 219 to the detection devices 201 to 207, which form a common detection device.

The system can furthermore comprise a video analysis system 221, which can indicate the behavior of a first goalkeeper and of a second goalkeeper as an application.

In order to be able to play a ball into the path of an attacker in a precisely targeted manner with a long punt from the hand, various partial skills of a goalkeeper (TW1) are advantageous. Firstly, this is the goalkeeper's ability to anticipate with regard to the expected position of a teammate at the instant of the acceptance of the ball by the teammate P1 in position 10. Furthermore, the goalkeeper, with regard to his technical level in respect of force and coordination, should be able to control the ball adequately with the following biomechanical influencing variables:

Linear momentum
Angular momentum (left, right)
Punt angle (horizontal, vertical)

The biomechanical influencing variables mentioned here, just like the movement of the goalkeeper, are detectable in real time in a manner known per se.

If the player P1 to whom the ball is to be passed then starts to run in a specific direction with the average velocity v at the instant t1, the system, on the basis of model assumptions that comprise deterministic biomechanical laws and can be stored in the database, can predict where the ball would land at the instant t2 if it is punted for example with previously known biomechanical input premises, so as to land near the player's foot at the instant t2. This target to be headed for in the form of a target disk can be projected onto the playing or training surface permanently or dynamically variably by the indication device 213. The goalkeeper could therefore be given a visualization of the target zone already before he finally punts the ball, by real-time feedback. Those parameters that influenced the resulting ball trajectory, with punt angle alpha or beta, momentum of the ball p, ball trajectory, etc., are likewise available with a short time delay (0.1 s-0.5 s). In real time, the system can also be used to indicate the target precision of the punt, for example within the target disk. In the learning or real-time feedback made, the goalkeeper can then decide on what basis the feedback should take place. For this purpose, the goalkeeper or trainer chooses between different applications (apps) on a tablet PC, PC, notebook, Smartphone or other indication apparatus. He can decide whether the desired/actual value deviation is effected on the basis of the statistical data material that the database contains about a goalkeeper about which the database contains data. Alternatively, he can also resort to a real-time training and learning unit with reference to different biomechanical models. He can then select whether the punt should be performed in a distance-optimized manner, in a precision-optimized manner or in a time-optimized manner.

Figure 3:
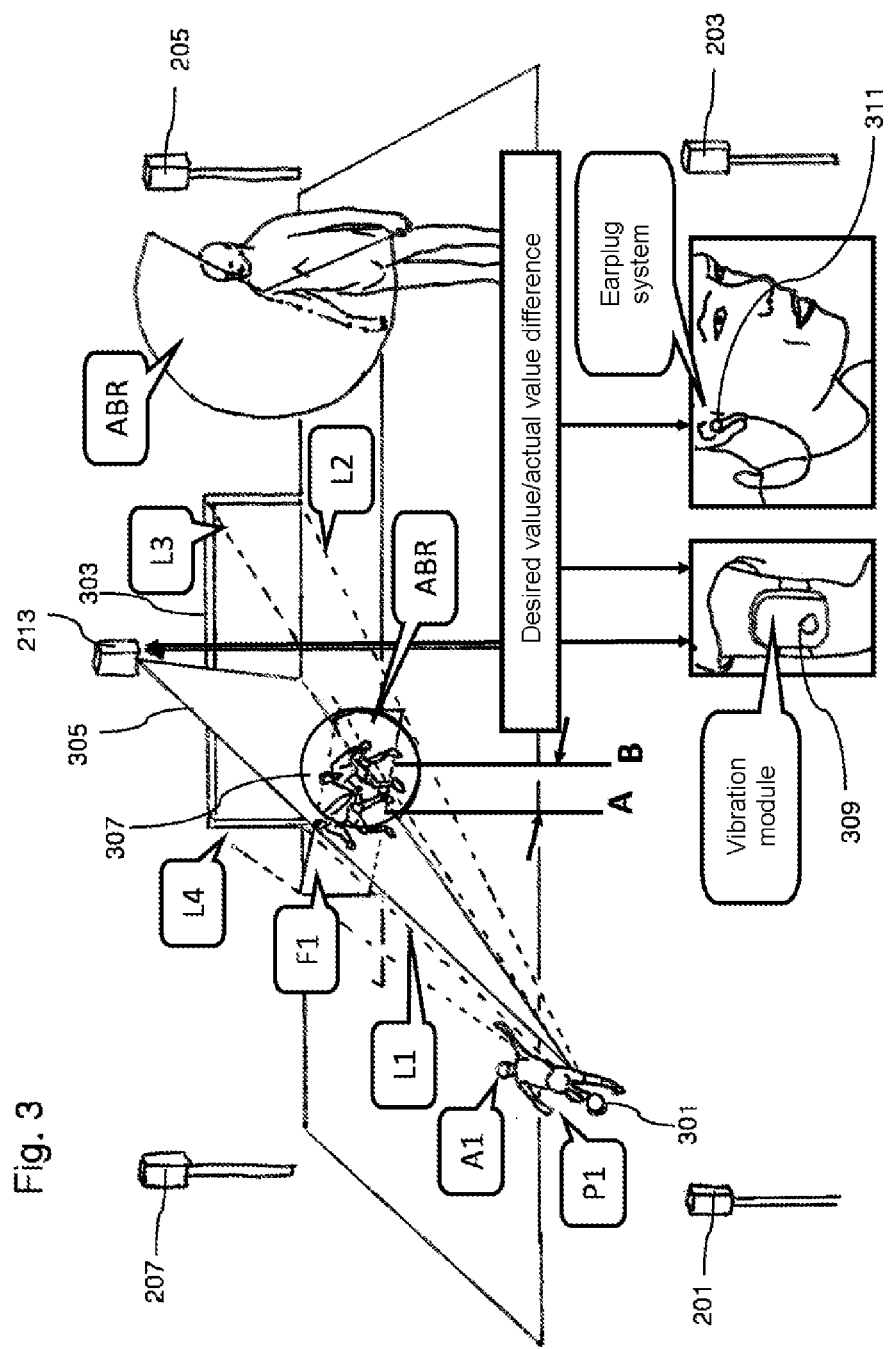
FIG. 3 shows a system for supporting a movement exercise in accordance with a further embodiment.

FIG. 3 shows a system for supporting a movement exercise with a playing object, for example with a soccer ball, in accordance with one embodiment. The system comprises at least one of the detection devices 201 to 207 depicted in FIG. 2. By way of example, these detect an actual position of a playing object 301, which may be a ball. The determination device, which is not depicted in FIG. 3, for example determines a connecting line 305 between the center of a goal and the actual position of the ball 301 on the basis of the actual position of the ball 301 and the center of a goal 303.

The indication device 213 can be embodied to project the connecting line 305 onto the playing area and indicate said line as desired position to a goalkeeper 307, who can be a playing object within the meaning of the present description in accordance with one embodiment.

In accordance with one embodiment, the indication device 213 can, alternatively or additionally, comprise at least one vibration module 309 indicating the direction toward the connecting line 305 to the goalkeeper. To this end, the goalkeeper can carry vibration modules on both sides, for example on the upper arms, and these can indicate vibration information relating to the direction of the connecting line 305 as a function of the actual position of the goalkeeper 307.

In accordance with one embodiment, the indication device 213 can alternatively or additionally comprise at least one loudspeaker 311 which, for example in the form of an earplug, can be attached to the ear of the goalkeeper, for example. The loudspeaker 311 is embodied to emit acoustic signals which provide information about the positioning of the desired position, i.e. which provide information about the positioning of the connecting line 305. In accordance with one embodiment, this renders it possible to dispense with the projection of the connecting line onto the playing area. In accordance with a different embodiment, it is possible for at least two of the aforementioned embodiments, for example projection and vibration or projection and acoustic signal, to be used together.

By way of example, if the attacker A1 shoots at the goal from the position P1, the ball, in the case of an approximately straight-line ball trajectory, for geometric reasons only enters the goal if it has moved within a space spanned between the ball and the imaginary connecting lines (L1-L4). The individual tactical object of the goalkeeper now consists in covering the largest possible area of the area (F1) by his posture and position with his anthropometrically determined range (ABR). He is most successful if he operates on the imaginary line between the center of the ball and the center of the goal. During shooting practice or the game, this line can be projected onto the playing area or training field by means of the indication device 213, which can form an optical-acoustic-tactile feedback system. Since the spatial position of the ball 301 can be transmitted to the system in real time, this line permanently moves with the ball position. Hence, via visual real-time feedback, the goalkeeper can permanently optimize his individual-tactical positioning. Parallel to the visual real-time feedback, there is acoustic feedback by means of a mini earplug system and/or a small loudspeaker system, which is attached to the body of the goalkeeper, and/or by means of a PA system. This audio feedback operates on the basis that, for example, the standard pitch a is played if the correct position is assumed and, in the case of an increasing desired/actual value difference (SID), the frequency is modified proportionally to the distance from the ideal position. In terms of acoustic feedback, the system could likewise work like echo sounding or like acoustic feedback from a parking assistance system, etc. The third component of the real-time feedback is performed in the form of a desired/actual value difference-controlled modification of the vibration frequency and/or amplitude of a tactile-acoustic feedback system, which is worn on the body of the goalkeeper and may be an element of the indication device 213.

Figure 4:
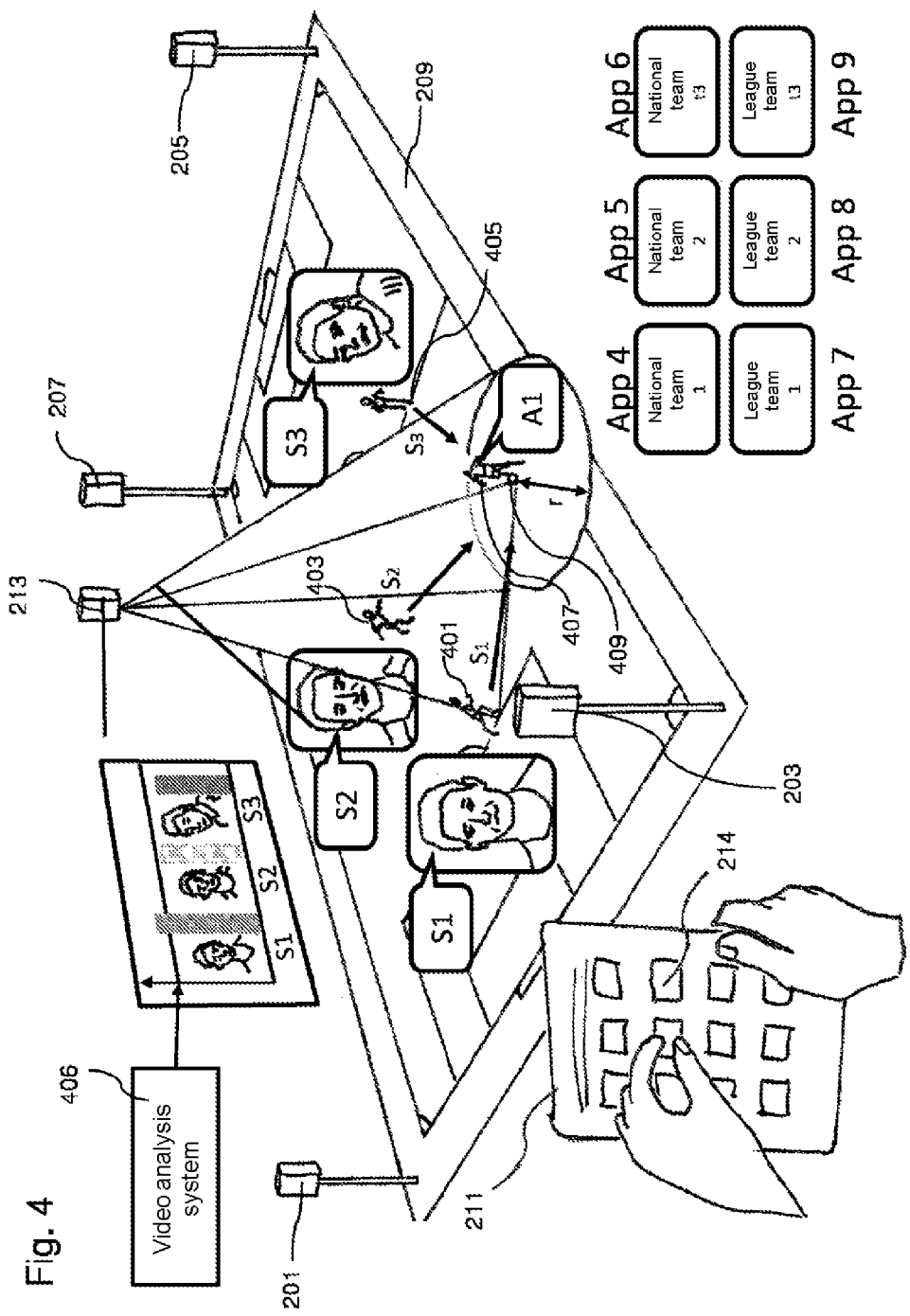
FIG. 4 shows a system for supporting a movement exercise in accordance with a further embodiment.

FIG. 4 shows a system for supporting a movement exercise in accordance with a further embodiment. Players 401 (S1), 403 (S2), 405 (S3) and 407 (A1) situated on the playing area 209 perform training with a ball 409 which, for example, is with player 407, who is the attacker. By way of example, players 401, 403 and 405 can be understood to be playing objects within the meaning of the present description. By way of example, the indication device 213 can produce signals which transmit a signal containing information relating to his/their desired position to players 401 to 405 or to only one of players 401, 403, 405. The information relating to the desired position can be indicated to the respective player 401, 403, 405 by visual or acoustic means, or by means of a vibration (tactile). To this end, the detection device 213 may have e.g. a vibration module or a loudspeaker, which can be attached to the respective players 401 to 405. The system can furthermore comprise a video analysis system 406.

The exemplary embodiment depicted in FIG. 4 elucidates the group tactic against the ball by means of so-called pressing.

In modern association soccer, defending already starts deep in the opposition half. By way of example, if an attacker of the opposing team (A1) comes into possession of the ball, the object of the opponents (S1-S3) surrounding him lies in attacking player A1 as aggressively as possible in order themselves to regain possession of the ball. This is referred to as pressing. The aggression with which a player performs pressing can be measured and assessed by means of the magnitude of the acceleration. If the database now comprises reference values with respect to the acceleration behavior in pressing situations for national and club teams and the world's best association soccer players, these can be employed for use in real-time feedback training, coaching and learning as desired values. The sequence in a real-time feedback training situation would be as follows in accordance with one embodiment:

1) On a tablet PC, Smartphone, PC notebook or any other setting and display unit of the determination device 211, a coach selects the reference values from the database which should be used for comparison in order to arrive at the desired/actual value differences. Apps 4, 5, 6 refer to the standard values of national teams and apps 7, 8, 9 refer to reference values of club teams.
2) By way of example, the coach holds a pushbutton in his hand, with which he can control the time at which pressing should be carried out by the training group. When the coach presses this pushbutton, the indication device 213 projects a light cone with radius r around the player with the ball; there likewise is an acoustic signal by means of the PA system and/or mini headphones and/or loudspeaker systems situated on the body. Additionally, depending on setup, there is also tactile feedback by means of a vibration system which can be controlled in terms of frequency and amplitude.
3) If one of the players now approaches the opponent with the ball with acceleration values which deviate too strongly from the reference values, this in turn can be reported back to the player by means of the above-described real-time feedback methods.
4) Once the activity is complete, the indication device 213 can project the desired values, actual values and the desired/actual value difference onto a surface and/or indicate the result on a tablet PC and/or a Smartphone or any other control and visualization unit.

Figure 5:
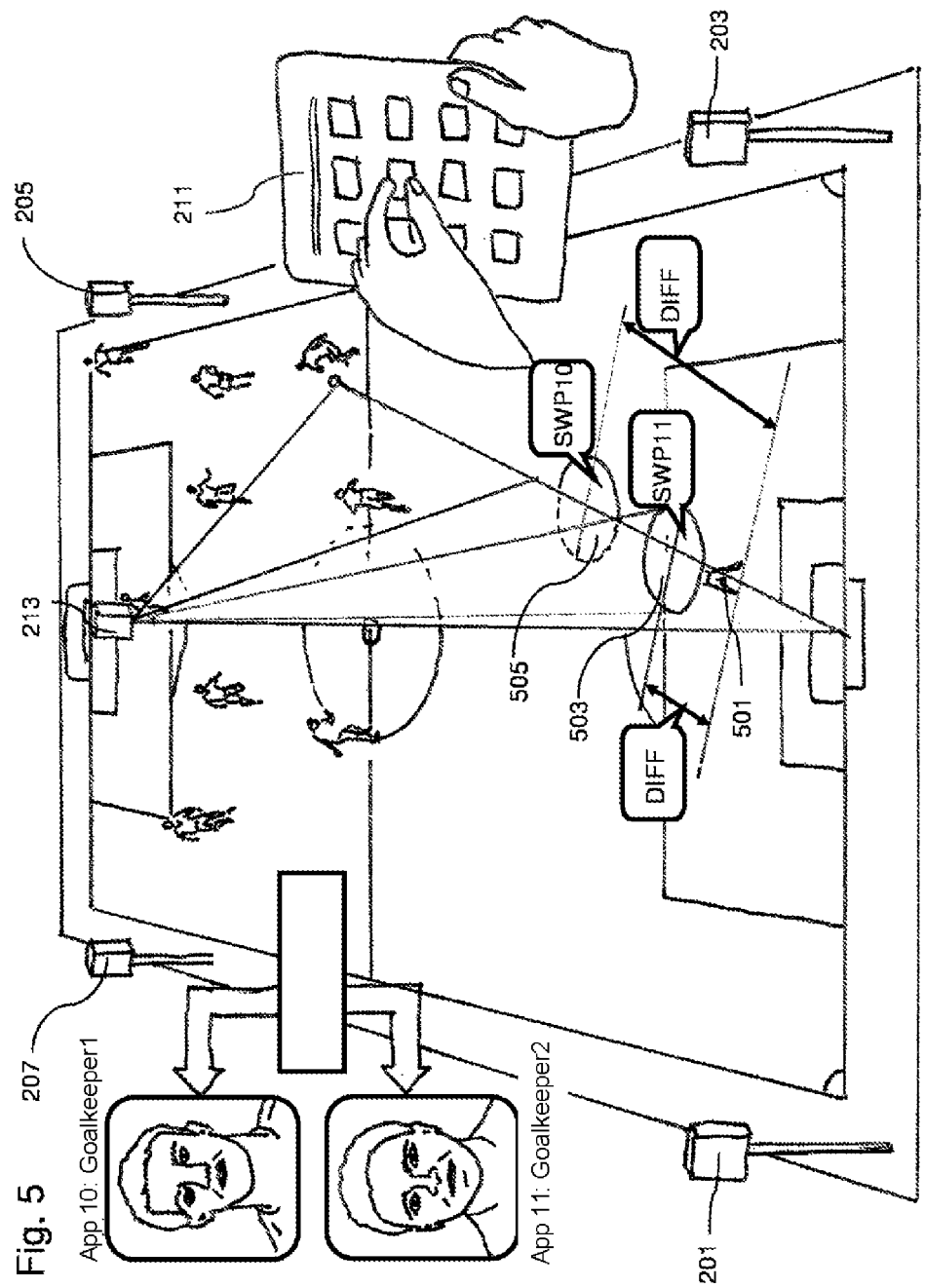
FIG. 5 shows a system for supporting a movement exercise in accordance with a further embodiment.

FIG. 5 shows a system in accordance with a further embodiment, in which e.g. a plurality of items of information relating to desired positions 503, 505 can be indicated to a goalkeeper 501.

In the modern game of association soccer, the goalkeeper should act as a playing-along goalkeeper behind the last line of defense. The basic rule that applies here is that the goalkeeper should move along the imaginary center of the goal-center of the ball connecting line. In a real-time feedback training or game scenario, this connecting line could now be projected permanently onto the playing or training area during the training or game by the indication device 213. By means of this real-time feedback projection, goalkeepers could learn very quickly to move on the imaginary goal-ball line. In addition to the visual feedback, there could also be acoustic and tactile feedback if the desired/actual value differences exceed certain limit values. The coach, or goalkeeper, for example has the option of deciding with respect to which statistical standard values stored in the database the desired/actual value difference is intended to be calculated. To this end, values which can be obtained in a manner known per se are stored in the database from the analysis of video sequences of the typical behavior of a certain goalkeeper. By way of example, the desired value position of the goalkeeper is determined in such a way that the mean distance between the goalkeeper and the geometric centroid of the team is established by empirical statistical methods, for example from 100 typical video scenes from the past, and stored in the database. This desired value is now put into a mathematical relationship with the centroid of the training or playing team, which is to be detected permanently, and the result is depicted visually in real time during the training or match. This is how the desired value position of the goalkeeper, which can be switched on by the app 10, would be projected dynamically in real time onto the playing area or training field in the form of a circular area (SWP 10). Analogously, the typical behavior of a different goalkeeper could also be depicted on the pitch in real time (SWP 11).

Figure 6:
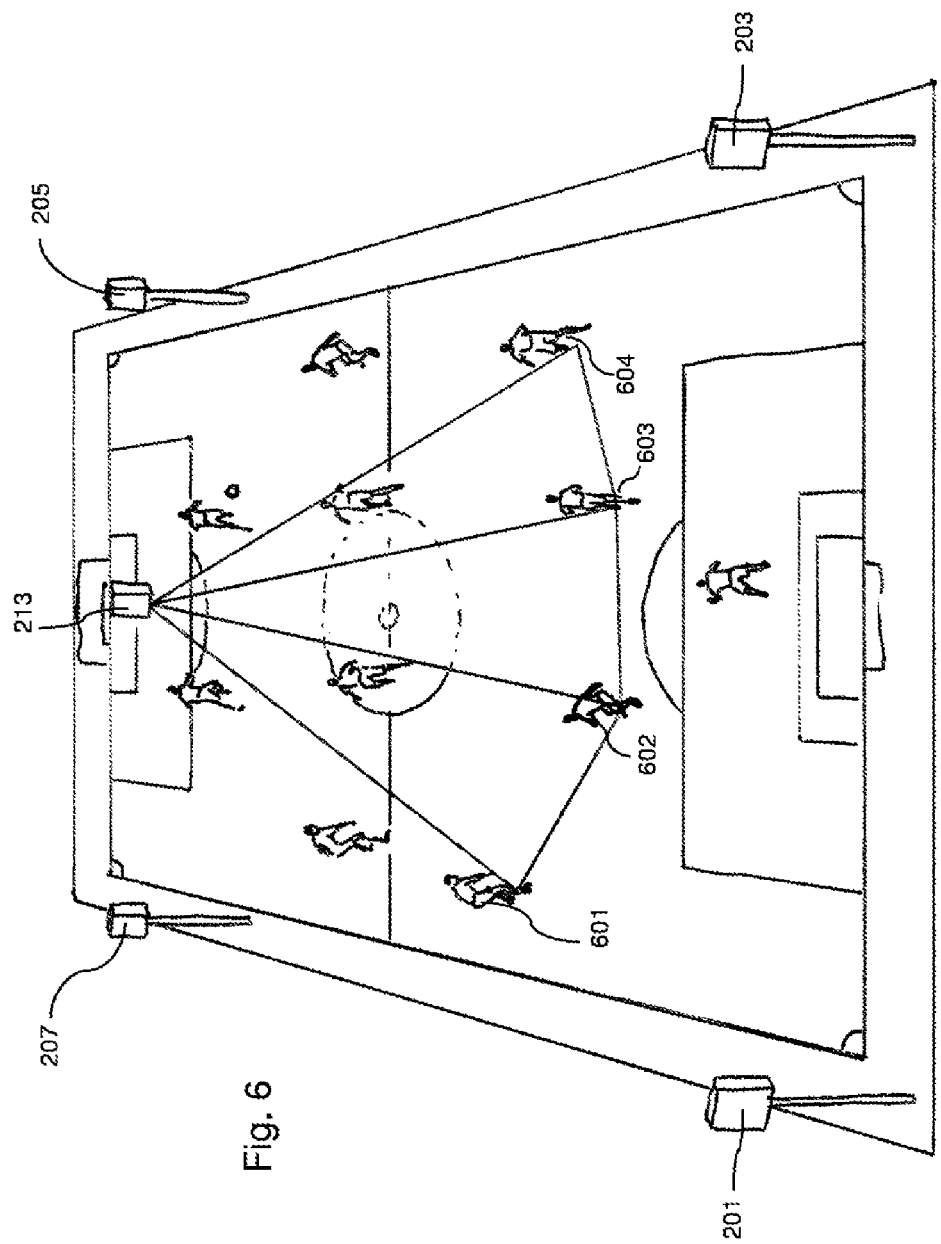
FIG. 6 shows a system for supporting a movement exercise in accordance with a further embodiment.

FIG. 6 shows a system in accordance with a further embodiment, in which players 601-604 are playing objects within the meaning of the present description. Here, information relating to the individual desired position as a function of actual positions of the remaining players is indicated to at least one or more of the players 601. By way of example, in this case, a centroid, for example a geometric centroid, can be determined from the actual positions of the remaining players in order to indicate an individual desired position to the respective player 601.

In accordance with one embodiment, the distance between the players can be monitored in this way. By way of example, the distance between player 601 and player 602 is too large, and so information can be output that this distance is to be reduced such that it corresponds to the desired distance as desired position. By way of example, the desired distance is predefined or emerges from model approaches, which may be deterministic and/or empirical statistical and which keep the desired positions of the players dynamically available in real time.

Figure 7:
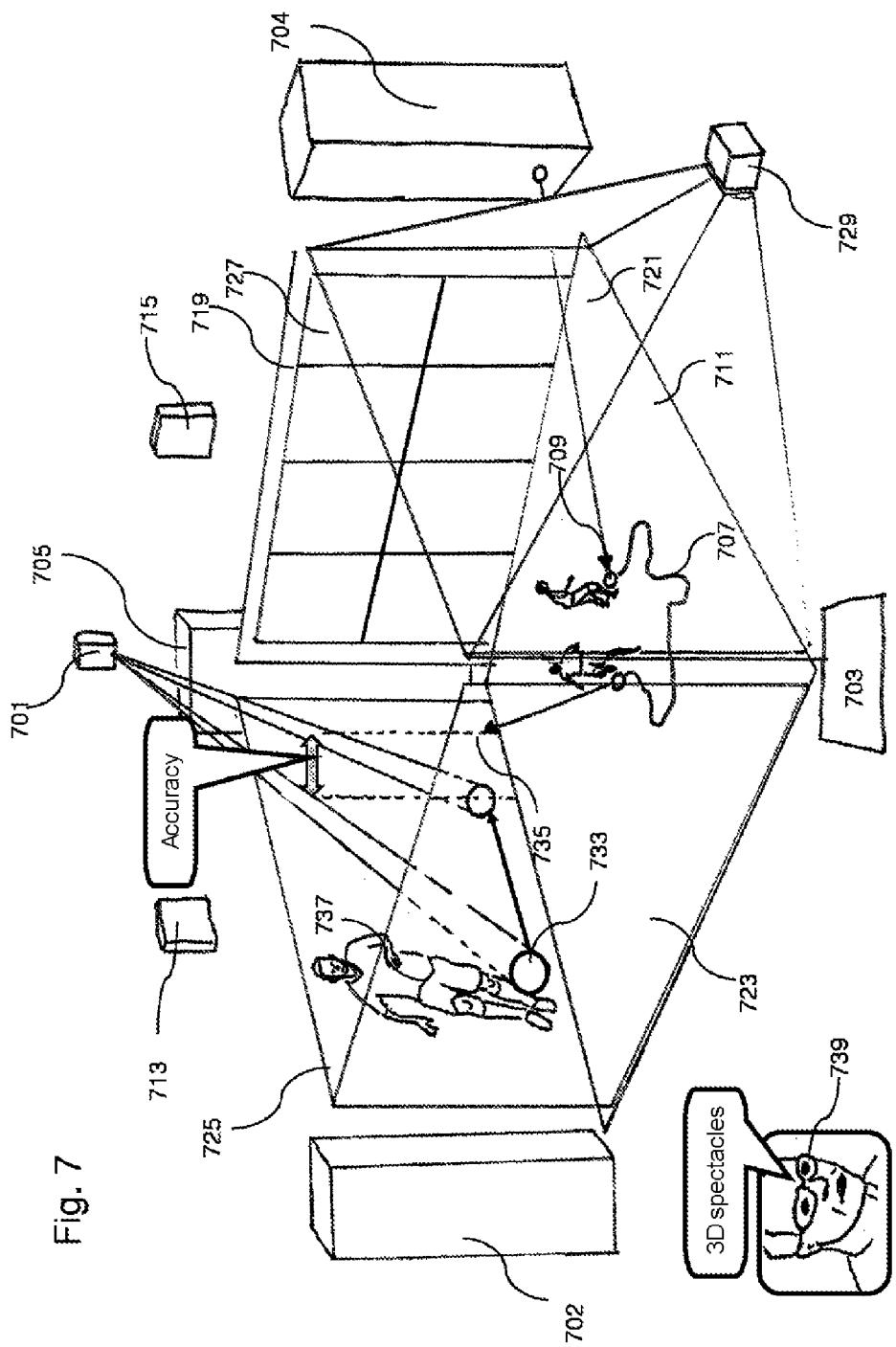
FIG. 7 shows a system for supporting a movement exercise in accordance with a further embodiment.

FIG. 7 shows a system in accordance with one embodiment which supports a movement exercise with a ball, for example with a soccer ball.

The system comprises at least one indication device 701, 729 and one or more ball providers 702, 703, 704 and 705, each designed to dispense a ball 709 toward the playing area 711. The system comprises at least one determination device 713, 715 designed to detect a position of the ball 709 as the actual position of the ball. For this purpose, the ball 709 can be designed to emit a transmission signal which the at least one determination device 713, 715 can receive for the purpose of position determination and can evaluate in a manner known per se. The at least one determination device 713, 715 can be designed, in particular, to detect a plurality of positions of the ball 709, which is illustrated by way of example by the trajectory 707 in FIG. 7. In this way, at least one determination device 713, 715 can detect a residence duration of the ball 709 at a player who receives and releases the ball 709. The residence duration can detect for example on the basis of a deceleration, i.e. a negative acceleration, of the ball 709 at the instant of the acceptance of the ball by the player and a positive acceleration at the instant of the release of the ball by the player.

The system furthermore comprises at least one ball catcher 719, 721, 723, 725 which is designed as a sensor wall, for example, which at least partly delimits the playing area 711. The sensor walls 719, 721, 723 and 725 comprise sensor regions 727, for example, which can be equipped with pressure sensors. For this purpose, an indication device 729 can choose a region 727, for example, in order to indicate a desired position of the ball 709. This can be effected for example by illumination of the respective region 727. In this way it is possible to indicate to the player where he should shoot the ball 709.

In accordance with an additional or alternative embodiment, the indication device 701 is provided, which is designed to statically or dynamically project a desired position 733 of the ball onto one of the sensor walls 725. The desired position can be variable, for example, as illustrated in FIG. 7, this being illustrated by the arrow. After the release of the ball, the sensor wall 725 can detect an impact location 735, for example by means of pressure technology, from which it is possible to determine a deviation 737 between the desired position and the detected position. The impact location 735 can be determined during a localization of the ball and a spatial geometry known to the computer even without pressure sensor technology. In this case, it is possible to dispense with the pressure sensor technology at the sensor wall.

In accordance with one embodiment, the indication device 701, 729 can project a playing figure 737 onto at least one of the sensor walls 719, 721, 723, 725 in order to simulate a teammate. This simulation can be three-dimensional, for which purpose the player can be equipped for example with three-dimensional lenses 739, for example 3D spectacles.

In accordance with one embodiment, a real-time localization system of one or more active or passive markers is provided, which can be fixed to one or more locations of one or more persons and/or of one or more playing objects. The real-time localization system comprises at least one indication device, for example. The real-time localization system can be an infrared cinematography system that functions with passive retroreflective markers, but it can also be a video-based tracking system, or a radio-based localization system, operating with active transmitters and corresponding receiver technology. However, it can also be any other active or passive localization system.

Furthermore, provision can be made of a real-time bio-signal recording and forwarding system for synchronously deriving and forwarding physiological signals, e.g. heart rate, heart rate variability, body temperature, respiratory frequency, skin conduction resistance, electrolyte composition, with the localization data mentioned above. Furthermore, technical data such as air pressure and/or rotation and/or acceleration can be taken into account.

Furthermore, a database system can be provided, which can be filled with external and/or internal data. Said database is permanently extended, either with external data or internal data. External data are for example data from games or training units or other events which have been recorded by video or some other data acquisition technique and analyzed. The database also holds values from other sources. For example performance-diagnostic characteristic variables from laboratory and/or field stage tests or else anthropometric data from measurement by means of a body scanner, etc. However, the database is also permanently and systematically extended by data implemented from the internal recordings (actual values). These data are designated as internal sources.

Furthermore, a control system can be provided, which is constantly extended by the implementation of expert knowledge. Experts can be sports scientists, sports physicians, engineers, soccer coaches, etc.

Furthermore, a set-up module can be provided, which is controlled by a PC or tablet PC or Smartphone or some other control unit. Said set-up module determines which internal and external sources are used for a training game or observation unit for the desired/actual value comparison. The specification for a real-time feedback system is likewise defined by means of the module.

The set-up module, the control system and the database system can be implemented in the determination device.

Furthermore, a real-time feedback system can be provided, which comprises the indication device and which transmits desired values and/or actual values and/or desired/actual value differences in real time to the subject or the subjects in the form of optical/visual and/or acoustic and/or tactile signals. Visual signals can be: a laser projection system or some other optical projection system or a screen or some other optical/visual representation method, an acoustic system, comprising miniature headphones or a PA system or a loudspeaker system situated on the body, or at least one vibration device which can be carried at defined locations on the body.

From the foregoing description, those skilled in the art can appreciate that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

The invention claimed is:

1. A system for detecting a user-dependent state of a sports object, comprising:
   a detection device comprising at least one of a detection signal transmitter and a detection signal receiver and configured to detect an actual position of the sports object;
   a determination device comprising a data receiver and a processor configured to determine a desired position of the sports object in a manner dependent on the actual position of the sports object; and an indication device configured to indicate a detected plurality of positions of the sports object and to indicate information relating to the desired position if the actual position differs from the desired position, wherein the determination device is configured to determine a predetermined position of the sports object as the desired position, and wherein the predetermined position is predefined with an aid of a rule.

2. The system of claim 1, wherein the user is equipped with a transmitter configured to transmit a signal that is received by the detection device.

3. The system of claim 1, wherein the state of the sports object is in at least one of: (i) residence duration of the sports object at a user, (ii) velocity of the sports object, (iii) momentum of the sports object, (iv) direction of movement of the sports object, and (v) acceleration of the sports object.

4. The system of claim 1, wherein the sports object comprises a transmitter configured to emit a position signal and wherein the detection signal receiver is configured to receive the emitted position signal to determine the actual position of the sports object.

5. The system of claim 1, wherein the detection signal transmitter is configured to transmit a signal that reflects off of the sports object and wherein the detection signal receiver is configured to receive the reflected signal, and in response, to determine the actual position of the sports object based upon the reflected reflection signal.

6. The system of claim 1, wherein the determination device is configured to determine a first instant of a user receiving the sports object and a second instant of the user releasing the sports object to determine a residence duration of the sports object with the user as the desired position of the sports object.

7. The system of claim 6, wherein the determination device is configured to determine a third instant of the user transferring the sports object between the first instant and the second instant, to determine a first sub-residence duration between the first instant and the third instant and a second sub-residence duration between the third instant and the second instant.

8. The system of claim 1, wherein the determination device is configured to determine an instant of an acceptance of the sports object by detection of a negative acceleration of the sports object with an aid of a temporal profile of the plurality of positions of the sports object.

9. The system of claim 1, wherein the determination device is configured to determine an instant of a release of the sports object by detection of a positive acceleration of the sports object with the aid of a temporal profile of the actual position of the sports object.

10. The system of claim 1 further comprises a sports object provider for dispensing the sports object.

11. The system of claim 1 further comprises a sports object catcher for catching the sports object after a sports object is released by the user.

12. The system as claimed in claim 11, wherein the sports object catcher is at least one of a ball goal and a sensor wall.

13. The system of claim 1, wherein the detection device is configured to store the detected plurality of positions.

14. The system of claim 1, wherein the indication device is configured to project a desired position onto a playing area.

15. The system claim 1, wherein the determination device is configured to compare the actual position with a desired position.

16. A method for detecting a user-dependent state of a sports object, comprising:
(i) detecting an actual position of the sports object by a detector comprising at least one of transmitting a detection signal and receiving a detection signal;
(ii) determining a desired position of the sports object in a manner dependent on the actual position of the sports object by a determination device configured to receiving data from the detector and processing the received data;
(iii) indicating a detected plurality of positions of the sports object; and
(iv) indicating information relating to the desired position if the actual position differs from the desired position,
wherein the determination device is configured to determine a predetermined position of the sports object as the desired position, and wherein the predetermined position is predefined with an aid of a rule.

17. The system of claim 3, wherein the velocity is at least one of translational velocity and rotational velocity, wherein the momentum is at least one of angular momentum and translational momentum, and the acceleration is at least one of positive acceleration and negative acceleration.

18. The system of claim 4, wherein the position signal is a global positioning signal.

19. The system of claim 5, wherein the detection signal transmitter is at least one of radar signal and a laser signal.

* * * * *